(12) United States Patent
Whirley et al.

(10) Patent No.: US 7,803,178 B2
(45) Date of Patent: Sep. 28, 2010

(54) INFLATABLE POROUS IMPLANTS AND METHODS FOR DRUG DELIVERY

(75) Inventors: Robert G. Whirley, Santa Rosa, CA (US); James M. Shapiro, San Francisco, CA (US)

(73) Assignee: TriVascular, Inc., Santa Rosa, CA (US)

( * ) Notice: Subject to any disclaimer, the term of this patent is extended or adjusted under 35 U.S.C. 154(b) by 0 days.

(21) Appl. No.: 10/769,532

(22) Filed: Jan. 30, 2004

(65) Prior Publication Data

US 2005/0171593 A1 Aug. 4, 2005

(51) Int. Cl.
*A61F 2/06* (2006.01)
(52) U.S. Cl. .................... 623/1.13; 623/1.21; 623/1.39; 623/1.42
(58) Field of Classification Search ................. 623/1.42, 623/1.43
See application file for complete search history.

(56) References Cited

U.S. PATENT DOCUMENTS

| | | | |
|---|---|---|---|
| 3,540,431 A | 11/1970 | Uddin | |
| 3,631,854 A | 1/1972 | Fryer | |
| 3,818,511 A | 6/1974 | Goldberg et al. | |
| 3,900,027 A | 8/1975 | Keedwell | |
| 3,902,198 A | 9/1975 | Rathjen | |
| 3,991,767 A | 11/1976 | Miller, Jr. et al. | |
| 4,140,126 A | 2/1979 | Choudhury | |
| 4,183,102 A | 1/1980 | Guiset | |
| 4,187,390 A | 2/1980 | Gore | |
| 4,208,745 A | 6/1980 | Okita | |
| 4,439,585 A | * 3/1984 | Gould et al. ................ 525/127 |
| 4,459,252 A | 7/1984 | MacGregor | |
| 4,474,630 A | 10/1984 | Planck et al. | |
| 4,497,074 A | 2/1985 | Rey et al. | |
| 4,550,447 A | 11/1985 | Seiler, Jr. et al. | |
| 4,552,707 A | 11/1985 | How | |
| 4,562,596 A | 1/1986 | Kornberg | |

(Continued)

FOREIGN PATENT DOCUMENTS

EP 0 407 566 A1 1/1990

(Continued)

OTHER PUBLICATIONS

Web page, "Drug Eluting Stents—Why Use Drug Eluting Stents?;" *Polymer Coatings Division*; at URL=http://www.lombardmedical. co.uk/lombard/pcde.why.html; Lombard Medical; printed Feb. 1, 2005.

(Continued)

*Primary Examiner*—Thomas J Sweet
(74) *Attorney, Agent, or Firm*—Hoffmann & Baron, LLP

(57) ABSTRACT

The present invention provides inflatable porous implants, such as grafts, stent-grafts, and bladders, as well as methods and kits for drug delivery. In particular, the grafts and stent-grafts of the present invention provide for the delivery of a therapeutic agent into a flow conduit in the body. The inflatable porous implants provide for direct delivery of larger, more precise dosages of drugs over longer administration periods into the body. Moreover, these inflatable porous implants are often flexible when inserted and have a low profile delivery configuration for easy placement. The implants of the present invention further provide a mechanical or structural function in addition to drug delivery in a single integrated structure.

34 Claims, 4 Drawing Sheets

U.S. PATENT DOCUMENTS

| | | |
|---|---|---|
| 4,580,568 A | 4/1986 | Gianturco |
| 4,592,754 A | 6/1986 | Gupte et al. |
| 4,617,932 A | 10/1986 | Kornberg |
| 4,647,416 A | 3/1987 | Seiler, Jr. et al. |
| 4,665,906 A | 5/1987 | Jervis |
| 4,705,517 A | 11/1987 | DiPisa, Jr. |
| 4,739,762 A | 4/1988 | Palmaz |
| 4,776,337 A | 10/1988 | Palmaz |
| 4,787,899 A | 11/1988 | Lazarus |
| 4,816,028 A | 3/1989 | Kapadia et al. |
| 4,941,870 A | 7/1990 | Okada et al. |
| 4,955,899 A | 9/1990 | Coma et al. |
| 4,957,669 A | 9/1990 | Primm |
| 5,100,422 A | 3/1992 | Berguer et al. |
| 5,104,399 A | 4/1992 | Lazarus |
| 5,104,400 A | 4/1992 | Berguer et al. |
| 5,108,424 A | 4/1992 | Hoffman, Jr. et al. |
| 5,122,154 A | 6/1992 | Rhodes |
| 5,123,917 A | 6/1992 | Lee |
| 5,151,105 A | 9/1992 | Kwan-Gett |
| 5,156,620 A | 10/1992 | Pigott |
| 5,207,695 A | 5/1993 | Trout, III |
| 5,219,355 A | 6/1993 | Parodi et al. |
| 5,275,622 A | 1/1994 | Lazarus et al. |
| 5,282,847 A | 2/1994 | Trescony et al. |
| 5,316,023 A | 5/1994 | Palmaz et al. |
| 5,330,528 A | 7/1994 | Lazim |
| 5,344,444 A | 9/1994 | Glastra |
| 5,354,310 A | 10/1994 | Garnic et al. |
| 5,360,443 A | 11/1994 | Barone et al. |
| 5,366,504 A | 11/1994 | Andersen et al. |
| 5,370,682 A | 12/1994 | Schmitt |
| 5,370,691 A | 12/1994 | Samson |
| 5,383,928 A | 1/1995 | Scott et al. |
| 5,387,235 A | 2/1995 | Chuter |
| 5,397,345 A | 3/1995 | Lazarus et al. |
| 5,405,379 A | 4/1995 | Lane |
| 5,411,550 A | 5/1995 | Herweck et al. |
| 5,423,851 A | 6/1995 | Samuels |
| 5,443,458 A | 8/1995 | Eury |
| 5,456,713 A | 10/1995 | Chuter |
| 5,464,419 A | 11/1995 | Glastra |
| 5,464,449 A | 11/1995 | Ryan et al. |
| 5,489,295 A | 2/1996 | Piplani et al. |
| 5,507,769 A | 4/1996 | Marin et al. |
| 5,507,770 A | 4/1996 | Turk |
| 5,522,880 A | 6/1996 | Barone et al. |
| 5,527,353 A | 6/1996 | Schmitt |
| 5,527,355 A | 6/1996 | Ahn |
| 5,529,653 A | 6/1996 | Glastra |
| 5,534,024 A | 7/1996 | Rogers et al. |
| 5,536,274 A | 7/1996 | Neuss |
| 5,554,180 A | 9/1996 | Turk |
| 5,562,724 A | 10/1996 | Vorwerk et al. |
| 5,562,726 A | 10/1996 | Chuter |
| 5,562,728 A | 10/1996 | Lazarus et al. |
| 5,571,079 A | 11/1996 | Bello et al. |
| 5,571,173 A | 11/1996 | Parodi |
| 5,575,817 A | 11/1996 | Martin |
| 5,578,071 A | 11/1996 | Parodi |
| 5,578,072 A | 11/1996 | Barone et al. |
| 5,591,229 A | 1/1997 | Parodi |
| 5,607,468 A | 3/1997 | Rogers et al. |
| 5,607,478 A | 3/1997 | Lentz et al. |
| 5,609,624 A | 3/1997 | Kalis |
| 5,609,625 A | 3/1997 | Piplani et al. |
| 5,609,628 A | 3/1997 | Keranen |
| 5,609,629 A | 3/1997 | Fearnot et al. |
| 5,628,783 A | 5/1997 | Quiachon et al. |
| 5,628,786 A | 5/1997 | Banas et al. |
| 5,628,788 A | 5/1997 | Pinchuk |
| 5,632,772 A | 5/1997 | Alcime et al. |
| 5,632,840 A | 5/1997 | Campbell |
| 5,653,746 A | 8/1997 | Schmitt |
| 5,662,700 A | 9/1997 | Lazarus |
| 5,665,115 A | 9/1997 | Cragg |
| 5,665,117 A | 9/1997 | Rhodes |
| 5,667,523 A | 9/1997 | Synon et al. |
| 5,669,936 A | 9/1997 | Lazarus |
| 5,676,671 A | 10/1997 | Inoue |
| 5,676,696 A | 10/1997 | Marcade |
| 5,676,697 A | 10/1997 | McDonald |
| 5,683,449 A | 11/1997 | Marcade |
| 5,683,451 A | 11/1997 | Lenker et al. |
| 5,683,453 A | 11/1997 | Palmaz |
| 5,693,084 A | 12/1997 | Chuter |
| 5,693,087 A | 12/1997 | Parodi |
| 5,693,088 A | 12/1997 | Lazarus |
| 5,697,968 A | 12/1997 | Rogers et al. |
| 5,700,285 A | 12/1997 | Myers et al. |
| 5,707,378 A | 1/1998 | Ahn et al. |
| 5,709,701 A | 1/1998 | Parodi |
| 5,709,703 A | 1/1998 | Lukie et al. |
| 5,713,917 A | 2/1998 | Leonhardt et al. |
| 5,716,395 A | 2/1998 | Myers et al. |
| 5,718,159 A | 2/1998 | Thompson |
| 5,718,973 A | 2/1998 | Lewis et al. |
| 5,720,776 A | 2/1998 | Chuter et al. |
| 5,723,004 A | 3/1998 | Dereume et al. |
| 5,733,325 A | 3/1998 | Robinson et al. |
| 5,735,892 A | 4/1998 | Myers et al. |
| 5,747,128 A | 5/1998 | Campbell et al. |
| 5,749,880 A | 5/1998 | Banas et al. |
| 5,749,920 A | 5/1998 | Quiachon et al. |
| 5,769,887 A | 6/1998 | Brown et al. |
| 5,785,679 A | 7/1998 | Abolfathi et al. |
| 5,788,626 A | 8/1998 | Thompson |
| 5,789,047 A | 8/1998 | Sasaki et al. |
| 5,800,512 A | 9/1998 | Lentz et al. |
| 5,800,518 A | 9/1998 | Piplani et al. |
| 5,824,039 A | 10/1998 | Piplani et al. |
| 5,824,044 A | 10/1998 | Quiachon et al. |
| 5,827,320 A | 10/1998 | Richter et al. |
| 5,843,069 A | 12/1998 | Butler et al. |
| 5,843,158 A | 12/1998 | Lenker et al. |
| 5,843,160 A | 12/1998 | Rhodes |
| 5,843,164 A | 12/1998 | Frantzen et al. |
| 5,843,167 A | 12/1998 | Dwyer et al. |
| 5,843,170 A | 12/1998 | Ahn |
| 5,855,598 A | 1/1999 | Pinchuk |
| 5,871,536 A | 2/1999 | Lazarus |
| 5,871,537 A | 2/1999 | Holman et al. |
| 5,906,641 A | 5/1999 | Thompson et al. |
| 5,926,650 A | 7/1999 | Suzuki et al. |
| 5,961,545 A | 10/1999 | Lentz et al. |
| 5,961,546 A | 10/1999 | Robinson et al. |
| 5,968,090 A | 10/1999 | Ratcliff et al. |
| 5,972,027 A | 10/1999 | Johnson |
| 5,972,441 A | 10/1999 | Campbell et al. |
| 5,976,179 A | 11/1999 | Inoue |
| 5,976,650 A | 11/1999 | Campbell et al. |
| 5,984,956 A | 11/1999 | Tweden et al. |
| 5,989,287 A | 11/1999 | Yang et al. |
| 5,993,481 A | 11/1999 | Marcade et al. |
| 5,997,573 A | 12/1999 | Quijano et al. |
| 6,001,123 A | 12/1999 | Lau |
| 6,004,346 A | 12/1999 | Wolff et al. |
| 6,004,347 A | 12/1999 | McNamara et al. |
| 6,004,348 A | 12/1999 | Banas et al. |
| 6,007,575 A | 12/1999 | Samuels |
| 6,015,429 A | 1/2000 | Lau et al. |
| 6,015,431 A | 1/2000 | Thornton et al. |
| 6,017,364 A | 1/2000 | Lazarus |
| 6,019,787 A | 2/2000 | Richard et al. |

| | | | | | | | |
|---|---|---|---|---|---|---|---|
| 6,025,044 | A | 2/2000 | Campbell et al. | 6,331,190 | B1 | 12/2001 | Shokoohi et al. |
| 6,027,811 | A | 2/2000 | Campbell et al. | 6,336,937 | B1 | 1/2002 | Vonesh et al. |
| 6,030,415 | A | 2/2000 | Chuter | 6,344,044 | B1 | 2/2002 | Fulkerson et al. |
| 6,036,702 | A | 3/2000 | Bachinski et al. | 6,344,054 | B1 | 2/2002 | Parodi |
| 6,036,723 | A | 3/2000 | Anidjar et al. | 6,352,553 | B1 | 3/2002 | van der Burg et al. |
| 6,039,755 | A | 3/2000 | Edwin et al. | 6,355,055 | B1 | 3/2002 | Waksman et al. |
| 6,042,605 | A | 3/2000 | Martin et al. | 6,355,056 | B1 | 3/2002 | Pinheiro |
| 6,051,020 | A | 4/2000 | Goicoechea et al. | 6,355,063 | B1 | 3/2002 | Calcote |
| 6,051,648 | A * | 4/2000 | Rhee et al. .................. 525/54.1 | 6,358,276 | B1 | 3/2002 | Edwin |
| 6,053,943 | A | 4/2000 | Edwin et al. | 6,361,780 | B1 | 3/2002 | Ley et al. |
| 6,059,823 | A | 5/2000 | Holman et al. | 6,364,856 | B1 | 4/2002 | Ding et al. |
| 6,063,114 | A | 5/2000 | Nash et al. | 6,368,355 | B1 | 4/2002 | Uflacker |
| 6,077,296 | A | 6/2000 | Shokoohi et al. | 6,379,381 | B1 | 4/2002 | Hossainy et al. |
| 6,090,128 | A | 7/2000 | Douglas | 6,379,382 | B1 | 4/2002 | Yang |
| 6,096,070 | A | 8/2000 | Ragheb et al. | 6,387,124 | B1 | 5/2002 | Buscemi et al. |
| 6,098,630 | A | 8/2000 | Papazoglou | 6,395,019 | B2 | 5/2002 | Chobotov |
| 6,102,938 | A | 8/2000 | Evans et al. | 6,398,803 | B1 | 6/2002 | Layne et al. |
| 6,102,940 | A | 8/2000 | Robichon et al. | 6,406,489 | B1 | 6/2002 | Richter et al. |
| 6,110,198 | A | 8/2000 | Fogarty et al. | 6,409,716 | B1 | 6/2002 | Sahatjian et al. |
| 6,124,523 | A | 9/2000 | Banas et al. | 6,409,756 | B1 | 6/2002 | Murphy |
| 6,126,685 | A | 10/2000 | Lenker et al. | 6,409,757 | B1 | 6/2002 | Trout et al. |
| 6,129,756 | A | 10/2000 | Kugler et al. | 6,423,089 | B1 | 7/2002 | Gingras et al. |
| 6,132,459 | A | 10/2000 | Piplani et al. | 6,423,090 | B1 | 7/2002 | Hancock |
| 6,139,572 | A | 10/2000 | Campbell et al. | 6,428,506 | B1 | 8/2002 | Simhambhatla et al. |
| 6,143,015 | A | 11/2000 | Nobles | 6,428,565 | B1 | 8/2002 | Wisselink |
| 6,146,416 | A | 11/2000 | Andersen et al. | 6,432,131 | B1 | 8/2002 | Ravenscroft |
| 6,149,665 | A | 11/2000 | Gabbay | 6,432,132 | B1 | 8/2002 | Cottone et al. |
| 6,149,682 | A | 11/2000 | Frid | 6,432,438 | B1 * | 8/2002 | Shukla ....................... 424/426 |
| 6,152,956 | A | 11/2000 | Pierce | 6,436,133 | B1 | 8/2002 | Furst et al. |
| 6,153,292 | A | 11/2000 | Bell et al. | 6,440,165 | B1 | 8/2002 | Richter et al. |
| 6,156,063 | A | 12/2000 | Douglas | 6,443,981 | B1 | 9/2002 | Colone et al. |
| 6,159,239 | A | 12/2000 | Greenhalgh | 6,451,050 | B1 | 9/2002 | Rudakov et al. |
| 6,159,565 | A | 12/2000 | Campbell et al. | 6,451,053 | B1 | 9/2002 | Dehdashtian et al. |
| 6,162,245 | A | 12/2000 | Jayaraman | 6,454,796 | B1 | 9/2002 | Barkman et al. |
| 6,162,246 | A | 12/2000 | Barone | 6,471,687 | B2 | 10/2002 | Butler et al. |
| 6,165,210 | A | 12/2000 | Lau et al. | 6,471,721 | B1 | 10/2002 | Dang |
| 6,165,211 | A | 12/2000 | Thompson | 6,471,980 | B2 | 10/2002 | Sirhan et al. |
| 6,165,212 | A | 12/2000 | Dereume et al. | 6,475,238 | B1 | 11/2002 | Fedida |
| 6,165,213 | A | 12/2000 | Goicoechea et al. | 6,482,166 | B1 | 11/2002 | Fariabi |
| 6,165,214 | A | 12/2000 | Lazarus | 6,482,227 | B1 | 11/2002 | Solovay |
| 6,183,504 | B1 | 2/2001 | Inoue | 6,485,513 | B1 | 11/2002 | Fan |
| 6,187,036 | B1 | 2/2001 | Shaolian et al. | 6,488,701 | B1 | 12/2002 | Nolting et al. |
| 6,197,049 | B1 | 3/2001 | Shaolian et al. | 6,488,705 | B2 | 12/2002 | Schmitt et al. |
| 6,203,568 | B1 | 3/2001 | Lombardi et al. | 6,491,719 | B1 | 12/2002 | Fogarty et al. |
| 6,210,435 | B1 | 4/2001 | Piplani et al. | 6,494,904 | B1 | 12/2002 | Love |
| 6,221,102 | B1 | 4/2001 | Baker et al. | 6,494,909 | B2 | 12/2002 | Greenhalgh |
| 6,235,050 | B1 | 5/2001 | Quiachon et al. | 6,500,203 | B1 | 12/2002 | Thompson et al. |
| 6,238,432 | B1 | 5/2001 | Parodi | 6,517,571 | B1 | 2/2003 | Brauker et al. |
| 6,240,616 | B1 | 6/2001 | Yan | 6,517,574 | B1 | 2/2003 | Chuter |
| 6,245,097 | B1 | 6/2001 | Inoue | 6,520,984 | B1 | 2/2003 | Garrison et al. |
| 6,245,102 | B1 | 6/2001 | Jayaraman | 6,521,284 | B1 | 2/2003 | Parsons et al. |
| 6,248,116 | B1 | 6/2001 | Chevillon et al. | 6,533,811 | B1 | 3/2003 | Ryan et al. |
| 6,251,133 | B1 | 6/2001 | Richter et al. | 6,537,195 | B2 | 3/2003 | Forman |
| 6,251,136 | B1 | 6/2001 | Guruwaiya et al. | 6,540,778 | B1 | 4/2003 | Quiachon et al. |
| 6,254,632 | B1 | 7/2001 | Wu et al. | 6,545,097 | B2 | 4/2003 | Pinchuk et al. |
| 6,264,684 | B1 | 7/2001 | Banas et al. | 6,554,857 | B1 | 4/2003 | Zilla et al. |
| 6,280,466 | B1 | 8/2001 | Kugler et al. | 6,554,858 | B2 | 4/2003 | Dereume et al. |
| 6,283,991 | B1 | 9/2001 | Cox et al. | 6,558,414 | B2 | 5/2003 | Layne |
| 6,287,330 | B1 | 9/2001 | Johansson et al. | 6,582,458 | B1 | 6/2003 | White et al. |
| 6,287,335 | B1 | 9/2001 | Drasler et al. | 6,599,275 | B1 | 7/2003 | Fischer, Jr. |
| 6,293,968 | B1 | 9/2001 | Taheri | 6,613,082 | B2 | 9/2003 | Yang |
| 6,293,969 | B1 | 9/2001 | Chuter | 6,613,083 | B2 | 9/2003 | Alt |
| 6,296,661 | B1 | 10/2001 | Davila et al. | 6,613,084 | B2 | 9/2003 | Yang |
| 6,302,908 | B1 | 10/2001 | Parodi | 6,616,650 | B1 | 9/2003 | Rowe |
| 6,306,165 | B1 | 10/2001 | Patnaik et al. | 6,652,570 | B2 | 11/2003 | Smith et al. |
| 6,312,462 | B1 | 11/2001 | McDermott et al. | 6,652,575 | B2 | 11/2003 | Wang |
| 6,315,791 | B1 | 11/2001 | Gingras et al. | 6,652,581 | B1 | 11/2003 | Ding |
| 6,316,522 | B1 | 11/2001 | Loomis et al. | 6,656,506 | B1 * | 12/2003 | Wu et al. .................... 424/489 |
| 6,319,278 | B1 | 11/2001 | Quinn | 6,663,662 | B2 * | 12/2003 | Pacetti et al. ............... 623/1.13 |
| 6,325,819 | B1 | 12/2001 | Pavcnik et al. | 6,752,829 | B2 | 6/2004 | Kocur et al. |
| 6,325,823 | B1 | 12/2001 | Horzewski et al. | 2001/0004705 | A1 | 6/2001 | Killion et al. |
| 6,328,762 | B1 | 12/2001 | Anderson et al. | 2001/0007955 | A1 | 7/2001 | Drasler et al. |
| 6,331,188 | B1 | 12/2001 | Lau et al. | 2001/0010013 | A1 | 7/2001 | Cox et al. |

| | | | | | | |
|---|---|---|---|---|---|---|
| 2001/0011188 A1 | 8/2001 | Berry et al. | | 2002/0198587 A1 | 12/2002 | Greenberg et al. |
| 2001/0014823 A1 | 8/2001 | Ressemann et al. | | 2002/0198588 A1 | 12/2002 | Armstrong et al. |
| 2001/0016770 A1 | 8/2001 | Allen et al. | | 2003/0004565 A1 | 1/2003 | Harnek et al. |
| 2001/0023370 A1 | 9/2001 | Smith et al. | | 2003/0009211 A1 | 1/2003 | DiCarlo |
| 2001/0027338 A1 | 10/2001 | Greenberg | | 2003/0009212 A1 | 1/2003 | Kerr |
| 2001/0027339 A1 | 10/2001 | Boatman et al. | | 2003/0028243 A1 | 2/2003 | Bates et al. |
| 2001/0029349 A1 | 10/2001 | Leschinsky | | 2003/0033004 A1 | 2/2003 | Ishii et al. |
| 2001/0029397 A1 | 10/2001 | Thompson | | 2003/0033007 A1 | 2/2003 | Sirhan et al. |
| 2001/0037142 A1 | 11/2001 | Stelter et al. | | 2003/0036794 A1 | 2/2003 | Ragheb et al. |
| 2001/0037147 A1 | 11/2001 | Lau et al. | | 2003/0060871 A1 | 3/2003 | Hill et al. |
| 2001/0039446 A1 | 11/2001 | Edwin et al. | | 2003/0074048 A1 | 4/2003 | Sherry |
| 2001/0041928 A1 | 11/2001 | Pavcnik et al. | | 2003/0074050 A1 | 4/2003 | Kerr |
| 2001/0044652 A1 | 11/2001 | Moore | | 2003/0074058 A1 | 4/2003 | Sherry |
| 2001/0047198 A1 | 11/2001 | Drasler et al. | | 2003/0093145 A1 | 5/2003 | Brown et al. |
| 2001/0049534 A1 | 12/2001 | Lachat | | 2003/0097174 A1 | 5/2003 | Henderson |
| 2001/0049550 A1 | 12/2001 | Martin et al. | | 2003/0120339 A1 * | 6/2003 | Banik et al. .................. 623/1.42 |
| 2001/0053929 A1 | 12/2001 | Vonesh et al. | | 2003/0125797 A1 | 7/2003 | Chobotov et al. |
| 2002/0002397 A1 | 1/2002 | Martin et al. | | 2003/0143330 A1 | 7/2003 | Lomis et al. |
| 2002/0007193 A1 | 1/2002 | Tanner et al. | | 2003/0216802 A1 | 11/2003 | Chobotov |
| 2002/0007212 A1 | 1/2002 | Brown et al. | | 2004/0030218 A1 * | 2/2004 | Kocur et al. .................. 600/36 |
| 2002/0016623 A1 | 2/2002 | Kula et al. | | 2004/0138734 A1 | 7/2004 | Chobotov et al. |
| 2002/0016626 A1 | 2/2002 | DiMatteo et al. | | 2004/0167614 A1 | 8/2004 | Anson |
| 2002/0016627 A1 | 2/2002 | Golds | | | | |
| 2002/0019665 A1 | 2/2002 | Dehdashtian et al. | | | FOREIGN PATENT DOCUMENTS | |
| 2002/0026231 A1 | 2/2002 | Shannon et al. | | | | |
| 2002/0026235 A1 | 2/2002 | Anderson et al. | | EP | 0 747 069 B1 | 8/1990 |
| 2002/0032408 A1 | 3/2002 | Parker et al. | | EP | 0 997 115 B1 | 11/1990 |
| 2002/0037145 A1 | 3/2002 | Irie et al. | | EP | 0 480 667 A1 | 4/1992 |
| 2002/0040236 A1 | 4/2002 | Lau et al. | | EP | 1 121 945 A1 | 12/1992 |
| 2002/0040237 A1 | 4/2002 | Lentz et al. | | EP | 0 617 930 A1 | 5/1994 |
| 2002/0042644 A1 | 4/2002 | Greenhalgh | | EP | 1 360 967 A1 | 2/1995 |
| 2002/0042645 A1 | 4/2002 | Shannon | | EP | 0 646 151 A1 | 4/1995 |
| 2002/0045931 A1 | 4/2002 | Sogard et al. | | EP | 0 646 365 A1 | 4/1995 |
| 2002/0045933 A1 | 4/2002 | Jang | | EP | 0 473 694 B1 | 12/1995 |
| 2002/0045934 A1 | 4/2002 | Jang | | EP | 0 689 806 A2 | 1/1996 |
| 2002/0045935 A1 | 4/2002 | Jang | | EP | 0 775 472 A3 | 5/1997 |
| 2002/0049487 A1 | 4/2002 | Lootz et al. | | EP | 1 029 518 A2 | 8/2000 |
| 2002/0049490 A1 | 4/2002 | Pollock et al. | | EP | 1 093 772 A2 | 4/2001 |
| 2002/0049493 A1 | 4/2002 | Jang | | EP | 0 821 646 B1 | 9/2001 |
| 2002/0052645 A1 | 5/2002 | Kugler et al. | | EP | 0 808 140 B1 | 12/2001 |
| 2002/0052649 A1 | 5/2002 | Greenhalgh | | EP | 1 208 817 A2 | 5/2002 |
| 2002/0055768 A1 | 5/2002 | Hess et al. | | EP | 1 212 987 A2 | 6/2002 |
| 2002/0065552 A1 | 5/2002 | Jayaraman et al. | | EP | 1 212 988 A2 | 6/2002 |
| 2002/0072792 A1 | 6/2002 | Burgermeister et al. | | EP | 0 877 582 B1 | 10/2002 |
| 2002/0082552 A1 | 6/2002 | Ding et al. | | EP | 1 148 843 B1 | 4/2003 |
| 2002/0082680 A1 | 6/2002 | Shanley et al. | | WO | WO 90/08801 A1 | 8/1990 |
| 2002/0082682 A1 | 6/2002 | Barclay et al. | | WO | WO 90/14055 | 11/1990 |
| 2002/0082685 A1 | 6/2002 | Sirhan et al. | | WO | WO 92/22604 A1 | 12/1992 |
| 2002/0091440 A1 | 7/2002 | Calcote | | WO | WO 95/03754 | 2/1995 |
| 2002/0096252 A1 | 7/2002 | Lukic | | WO | WO 95/09585 | 4/1995 |
| 2002/0098278 A1 | 7/2002 | Bates et al. | | WO | WO 95/09586 | 4/1995 |
| 2002/0099434 A1 | 7/2002 | Buscemi et al. | | WO | WO 95/11720 | 5/1995 |
| 2002/0099436 A1 | 7/2002 | Thornton et al. | | WO | WO 95/16406 | 6/1995 |
| 2002/0103527 A1 | 8/2002 | Kocur et al. | | WO | WO 96/24308 | 8/1996 |
| 2002/0107561 A1 | 8/2002 | Pinheiro | | WO | WO 96/28115 | 9/1996 |
| 2002/0111665 A1 | 8/2002 | Lauterjung | | WO | WO 97/07751 | 6/1997 |
| 2002/0116048 A1 | 8/2002 | Chobotov | | WO | WO 97/25938 | 7/1997 |
| 2002/0116051 A1 | 8/2002 | Cragg | | WO | WO 97/27820 | 8/1997 |
| 2002/0120326 A1 | 8/2002 | Michal | | WO | WO 97/33533 | 9/1997 |
| 2002/0120327 A1 | 8/2002 | Cox et al. | | WO | WO 97/37616 | 10/1997 |
| 2002/0123790 A1 | 9/2002 | White et al. | | WO | WO 97/41804 | 11/1997 |
| 2002/0133221 A1 | 9/2002 | Schatz | | WO | WO 98/06355 | 2/1998 |
| 2002/0138048 A1 | 9/2002 | Tuch | | WO | WO 98/10806 | 3/1998 |
| 2002/0138129 A1 | 9/2002 | Armstrong et al. | | WO | WO 98/12989 | 4/1998 |
| 2002/0156518 A1 | 10/2002 | Tehrani | | WO | WO 98/27894 | 7/1998 |
| 2002/0156521 A1 | 10/2002 | Ryan et al. | | WO | WO 98/30156 | 7/1998 |
| 2002/0156522 A1 | 10/2002 | Ivancev et al. | | WO | WO 98/33453 | 8/1998 |
| 2002/0165602 A1 | 11/2002 | Douglas et al. | | WO | WO 98/38708 | 8/1998 |
| 2002/0165603 A1 | 11/2002 | Thornton et al. | | WO | WO 98/38947 | 9/1998 |
| 2002/0169499 A1 | 11/2002 | Zilla et al. | | WO | WO 98/41167 | 9/1998 |
| 2002/0173836 A1 | 11/2002 | Pinchuk | | WO | WO 98/44870 | 10/1998 |
| 2002/0173837 A1 | 11/2002 | Lauterjung | | WO | WO 98/44873 | 10/1998 |
| 2002/0193872 A1 | 12/2002 | Trout et al. | | WO | WO 98/55047 | 12/1998 |

| | | |
|---|---|---|
| WO | WO 99/00073 | 1/1999 |
| WO | WO 99/11199 | 3/1999 |
| WO | WO 99/32051 | 7/1999 |
| WO | 9939662 | 8/1999 |
| WO | WO 99/38455 | 8/1999 |
| WO | WO 99/39662 | 8/1999 |
| WO | WO 99/39663 | 8/1999 |
| WO | WO 99/47078 | 9/1999 |
| WO | WO 99/65419 | 12/1999 |
| WO | WO 00/10487 | 3/2000 |
| WO | WO 00/33769 | 6/2000 |
| WO | WO 00/42947 | 7/2000 |
| WO | WO 00/42948 | 7/2000 |
| WO | WO 00/44808 A1 | 8/2000 |
| WO | WO 00/45741 | 8/2000 |
| WO | WO 00/51522 | 9/2000 |
| WO | WO 00/53251 | 9/2000 |
| WO | WO 01/01867 A1 | 1/2001 |
| WO | WO 01/01886 A1 | 1/2001 |
| WO | WO 01/15633 A1 | 3/2001 |
| WO | WO 01/21107 | 3/2001 |
| WO | WO 01/21108 | 3/2001 |
| WO | WO 01/26456 A1 | 4/2001 |
| WO | WO 01/21102 | 5/2001 |
| WO | WO 01/30270 A2 | 5/2001 |
| WO | WO 01/39700 A1 | 6/2001 |
| WO | 0152914 | 7/2001 |
| WO | WO 01/52771 A1 | 7/2001 |
| WO | WO 01/52914 A1 | 7/2001 |
| WO | WO 01/66037 A2 | 9/2001 |
| WO | WO 01/66038 A2 | 9/2001 |
| WO | WO 01/67993 A2 | 9/2001 |
| WO | WO 01/74270 A2 | 10/2001 |
| WO | WO 01/92584 A1 | 12/2001 |
| WO | WO 02/100454 A1 | 12/2002 |
| WO | WO 03/003946 A1 | 1/2003 |
| WO | 03032869 | 4/2003 |
| WO | WO 03/026713 A1 | 4/2003 |
| WO | 03043539 | 5/2003 |
| WO | WO 03/043539 A1 | 5/2003 |
| WO | WO 03/053495 A2 | 7/2003 |
| WO | WO 03/082360 A1 | 10/2003 |
| WO | WO 03/094795 A1 | 11/2003 |
| WO | WO 03/094797 A1 | 11/2003 |
| WO | WO 03/094799 A1 | 11/2003 |
| WO | WO 2004/004603 A1 | 1/2004 |

OTHER PUBLICATIONS

Blum, et al., "Endoluminal stant-grafts for Infrarenal abdominal aortic aneurysms," *N Engl J Med*, 336(1):13-20, (1997).

Ernst, "Current therapy for infrarenal aortic aneurysms," *N Engl J Med*, 336(1):59-60, (1997).

Greenwald et al., "Highly Water Soluble Taxol Derivatives: 7-Polyethylene Glycol Carbamates and Carbonates:", J.Org.Chem., vol. 60, No. 2, pp. 331-336, 1995.

Haimovitch, L. and Patterson, N., "Robust growth is forecast for endovascular repair of AAAs," *The BBI Newsletter*, vol. 28, No. 5, pp. 113-144, (May 2003).

J.M. Harris, "Laboratory Synthesis of Polyethylene Glycol Derivatives," Journal of Macromolecular Science-Reviews in Macromolecular Chemistry, vol. C-25, No. 3, pp. 325-373, Jan. 1, 1985.

J.M. Harris, Ed., "Biomedical and Biotechnical Applications of Poly(Ethylene Glycol) Chemistry", Plenum, New York, pp. 1-14, 1992.

Matsushima et al., "Modification of *E. coli* Asparaginase with 2,4-Bis(O-Methoxypolyethylene Glycol)-6-Chloro-S-Triazine (Activated $PEG_2$); Disappearance of Binding Ability Towards Anti-Serum and Retention of Enzymic Activity," Chemistry Letters, pp. 773-776, 1980.

Moore, et al., "Transfemoral endovascular repair of abdominal aortic aneurysm: results of the North American EVT phase 1 trial," *J Vasc Surg*, 23(4):543-553, (1996).

Nathan et al., "Copolymers of Lysine and Polyethylene Glycol: A New Family of Functionalized Drug Carriers," Bioconjugate Chem. 4, 54-62 (1993).

Parodi, "Endovascular repair of abdominal aortic aneurysms and other arterial lesions," *J Vasc Surg*, 21(4):549-557, (1995).

Parodi, et al., "Transfemoral intraluminal graft implantation for abdominal aortic aneurysms," *Ann Vasc Surg*, 5(6):491-499, (1991).

U.S. Appl. No. 10/384,103, filed Mar. 6, 2003.
U.S. Appl. No. 10/461,853, filed Jun. 13, 2003.
U.S. Appl. No. 10/691,849, filed Oct. 22, 2003.
U.S. Appl. No. 60/534,638, filed Jan. 7, 2004.

Supplemental Search Report for a counterpart foreign application dated Jul. 23, 2008.

\* cited by examiner

INFLATABLE POROUS IMPLANTS AND METHODS FOR DRUG DELIVERY

BACKGROUND OF THE INVENTION

1. Field of the Invention

The present invention relates generally to medical devices and methods. More particularly, the present invention provides inflatable porous implants, such as grafts, stent-grafts, and bladders, as well as methods and kits for drug delivery.

Disorders of vessels and organs have created a need for prosthetic grafts or stent-grafts to repair or replace the function of the diseased vessels and organs. Of particular interest to the present invention are prosthetic devices that provide for the treatment of disease or injury that potentially compromises the integrity of a flow conduit in the body. For example, the prosthetic devices are useful in treating indications in the cardiovascular system, including thoracic and abdominal aortic aneurysms, arterial dissections (such as those caused by traumatic injury), etc. as well as indications in the digestive system (bile ducts, esophagus, and like structures in the gastrointestinal tract), respiratory system (bronchi, trachea, and the like), reproductive system (fallopian tubes, uterus, and the like), urinary system (urethral, ureteral, and the like), and other systems of the human body. The prosthetic grafts or stent-grafts reestablish or recreate the natural flow of the vessel or organ to be repaired, replaced, or bypassed.

While prosthetics grafts or stent-grafts have enjoyed some degree of success, enhancements to such implantable devices would be advantageous. In particular, one improvement is providing direct delivery of a therapeutic agent into the flow conduit in the body via the implantable prosthetic. In some instances, grafts for abdominal aortic aneurysms or other blood vessel aneurysms may suffer from complications such as thrombosis formation which may lead to occlusion of the graft; stent-grafts in general may provoke hyperplasia, which in turn may lead to failure of the graft. In such instances, the delivery of a therapeutic agent to treat or prevent such complications is especially useful.

To meet this need, various types of implantable devices have been designed to deliver agents directly into flow conduits in the body. Local delivery of therapeutic agents is advantageous over systemic administration for several reasons. First, local delivery enables appropriate dosages of the therapeutic agent to be achieved at a target site without subjecting other non-target vessels or organs to such agents. Second, the local concentration of the therapeutic agent can be much higher than can normally be achieved by systemic administration. Third, local delivery allows the therapeutic agent to focus on target tissue that might otherwise be slow to absorb the agent.

Direct administration of therapeutic agents primarily has been accomplished through the use of catheter injection or coated prosthetic devices. Direct administration of a therapeutic agent through a catheter typically requires that the catheter be in place in the body for the entire duration of drug delivery. As such, catheter injection treatment primarily is suited for short duration treatments. Coated prosthetic devices, such as stents, grafts, or other implants, are also widely utilized. While such coatings have achieved varying levels of success, some drawbacks are apparent. In particular, coating prosthetic devices involves a complex manufacturing process and in some instances the coating may be abraded off during assembly (e.g., passage of a stent through a delivery catheter or sheath) or deployment of the prosthetic. Another concern related to coated prosthetic devices is that the dosage amount, precision, and duration of drug delivery may also be limited by the coating itself, which typically represents a small fraction of a total mass of the implant.

For theses reasons, it is desirable to provide improved implantable devices and methods for delivering a therapeutic agent into a flow conduit in the body. In particular, it is desirable to provide improved implantable devices and methods that directly deliver larger, more precise doses of drugs over longer administration periods into the body. It is further desirable to provide implantable devices that are flexible and have a small profile for easy placement. It is still further desirable to provide integrated implantable devices that serve a mechanical or structural function in addition to drug delivery.

2. Description of the Background Art

Methods and apparatus for releasing active substances from implantable and other devices are described in U.S. Pat. Nos. 6,652,581; 6,652,575; 6,616,650; 6,613,084; 6,613,083; 6,613,082; 6,599,275; 6,554,857; 6,545,097; 6,537,195; 6,521,284; 6,471,980; 6,471,687; 6,409,716; 6,387,124; 6,379,382; 6,379,381; 6,364,856; 6,361,780; 6,358,276; 6,355,063; 6,355,055; 6,328,762; 6,316,522; 6,306,165; 6,254,632; 6,251,136; 6,240,616; 6,165,210; 6,096,070; 6,004,346; 5,972,027; 5,843,069; 5,609,629; 5,443,458; 5,411,550; 5,383,928; U.S. Publication Nos. 2003/0143330; 2003/0074048; 2003/0060871; 2003/0036794; 2003/0033007; 2003/0033004; 2003/0028243; 2003/0004565; 2002/0138048; 2002/0120326; 2002/0103527; 2002/0099434; 2002/0098278; 2002/0091440; 2002/0082685; 2002/0082682; 2002/0082680; 2002/0082552; 2002/0042645; 2002/0037145; 2002/0026235; 2001/0041928; PCT Publication Nos. WO 2004/004603 A1; WO 03/082360 A1; WO 03/043539 A1; WO 03/026713A1; WO 01/52914 A1; EP Patent Application Nos. EP 1 360 967 A1; EP 1 121 945 A1; EP 0 997 115 B1; EP 0 747 069 B1.

The full disclosures of each of the above-mentioned references are incorporated herein by reference.

BRIEF SUMMARY OF THE INVENTION

The present invention provides inflatable porous implants, such as grafts, stent-grafts, and bladders, as well as methods and kits for drug delivery. In particular, the grafts and stent-grafts of the present invention provide for the delivery of a therapeutic and/or diagnostic agent into a flow conduit in the body. The inflatable porous implants may provide for direct delivery of larger, more precise dosages of drugs over longer administration periods into the body. Moreover, these inflatable porous implants are often flexible when inserted and have a low profile delivery configuration for easy placement. The implants of the present invention may further provide a mechanical or structural function in addition to drug delivery in a single integrated structure as will be described in detail below.

The inflatable porous grafts and stent-grafts of the present invention are capable of repairing, replacing, or bypassing a diseased flow conduit or portion thereof in the body. Typically, such grafts and stent-grafts are implantable in any blood vessel in the patient's vasculature, including arteries (such as the aorta), veins, as well as in previously implanted grafts, shunts, fistulas, and the like. In such instances, the prosthetic devices are useful in treating several indications in the vascular system, including thoracic and abdominal aortic aneurysms, arterial dissections, thoracic or peripheral arterial aneurysms, other blood vessel aneurysms, vascular diseases, other diseased or anomalous blood vessels, diseased saphenous vein grafts in coronary arteries, etc. However, it will be appreciated that the devices of the present invention are not limited to deployment and/or implantation in the vasculature. For example, the grafts and stent-grafts of the present invention may be useful in treating other indications in the digestive system (bile ducts, esophagus, and like structures in the gastrointestinal tract), respiratory system (bronchi, trachea, and the like), reproductive system (fallopian tubes, uterus, and the like), urinary system (urethral, ureteral, and the like) and other systems of the human body.

In one aspect of the present invention, a graft comprises a graft body section and an inflation medium. The graft body has a proximal end, a distal end, and defines at least one inflatable porous channel or cavity. The inflation medium includes at least one therapeutic agent configured to be introduced into the inflatable channel. Exemplary grafts that may be utilized with the present invention are described in detail in U.S. Pat. No. 6,395,019 and co-pending U.S. patent application Ser. No. 10/327,711, both of which are assigned to the assignee of the present application and incorporated herein by reference. Other grafts may be utilized with the present invention; for instance, those described in U.S. Pat. No. 5,871,537 to Holman et al., U.S. Pat. No. 5,151,105 to Kwan-Gett, U.S. Pat. No. 5,156,620 to Pigott, U.S. Pat. No. 6,007,575 to Samuels, U.S. Pat. No. 6,312,462 to McDermott et al, and U.S. patent application Ser. No. 09/978,383 to Sherry (filed Oct. 16, 2001), the entirety of each is incorporated herein by reference.

The at least one therapeutic agent is capable of being transported from the inflation medium through a wall of the porous channel and released into a body lumen, such as a blood vessel in the patient's vasculature. The at least one agent may be configured to be released into the body from either a luminal or abluminal surface of the graft body section. The at least one agent may comprise a variety of agents that serve any therapeutic purpose depending on the particular indication being treated by the graft. For example, the agent may comprise one or more agents selected from the group consisting of an endothelialization promoting agent, an angiogenesis promoting agent, an anti-thrombotic agent, an anti-aneurysmal agent, an anti-infection agent, an anti-inflammatory agent, an anti-restenosis agent, a chemotherapeutic agent, and an anti-cancer agent.

The porous channel may have varying levels of porosity so as to provide for controlled and/or programmed drug delivery into the body lumen. The graft body section may comprise any biocompatible material capable of providing transport across its surface. For example, the graft body section may comprise one or more materials selected from the group consisting of a fluoropolymer, a polyethyleneterephthalate, a polyvinylchloride, a polyurethane, a polyolefin, and a polyamide. The graft body section may specifically comprise expanded polytetrafluoroethylene, perforated polytetrafluoroethylene, or other synthetic material. Methods and devices for manufacturing such grafts are described in more detail in International Patent Application No. PCT/US02/40997, assigned to the assignee of the present application and incorporated herein by reference.

The at least one channel may comprise one or more features selected from the group consisting of helical spirals, longitudinal or linear channels, and circumferential rings that may extend between the graft ends, just a portion of a length of the graft, or just around the distal or proximal ends of the graft. Other orientations such as interconnecting grids or rings, serrated patterns, staggered or discontinuous patterns, non-linear or wave-type patterns may also be suitable alone or in combination with the above-mentioned channel configurations. Further, the graft may also comprise at least one inflatable porous cuff disposed at the proximal end, distal end, or both ends of the graft body section and optionally may be in fluid communication with the at least one channel and containing the inflation medium. The one or more channels and cuffs provide a sufficiently stiff structure when inflated, which helps to support the graft body section and serves to recreate or reestablish a natural flow conduit in the body. Additionally, the one or more inflated channels and cuffs may provide a conformable surface to seal the graft against any leaks and may help to prevent kinking of the device. Kink-resistant grafts and endoleak management is described in more detail co-pending U.S. patent application Ser. Nos. 10/384,103 and 10/691,849, respectively, both of which are assigned to the assignee of the present application and incorporated herein by reference.

The inflation medium typically but not necessarily comprises a therapeutic agent-carrying host polymer. The therapeutic agent is released from the polymer in a controlled fashion. The therapeutic agent is capable of being released by diffusion through the host polymer or alternatively by degradation or decomposition of the host polymer. In the case of polymer release via degradation, the graft body section comprises biocompatible material capable of inhibiting transport of a bulk of the host polymer. In general, porosity of the channel and/or diffusion or degradation characteristics of the host polymer may be modified to achieve a desired release rate for the therapeutic agent. Typically, the quantity of agent releasable into the body lumen ranges in the microgram to milligram levels, roughly from about 10 micrograms to about 100 milligrams or more. The therapeutic agent is configured to be transported into a body lumen in a time period ranging from about less than a week to about several or many months, roughly from about seven days to about twelve months.

The host polymer may generally comprise any biocompatible material that is capable of being introduced into the inflatable channel before, during, or after graft deployment and/or implantation. For example, the host polymer may be used to inflate the graft after it has been deployed from a delivery catheter but prior to actual implantation in the situs. The host polymer may comprise one or more materials selected from the group consisting of polyethylene glycol, polyethylene glycol diacrylate, ethoxylated trimethylolpropane triacrylate, pluronic polyoxymer, acrylamide, polyethylene oxide, polyvinyl alcohol, polyethylene-co-vinyl alcohol, polyacrylic acid, polyethylene-co-acrylic acid, polyethyloxazoline, polyvinyl pyrrolidone, polyethylene-co-vinyl pyrrolidone, polymaleic acid, polyethylene-co-maleic acid, polyacrylamide, and polyethylene oxide-co-polypropylene oxide. The inflation medium may comprise a liquid and may either remain a liquid after injection or may thereafter solidify due to a phase change or formation of cross-links. In the latter case, the inflation medium may comprise a curable liquid having a cure time ranging from about three minutes to about twenty minutes and a post-cure elastic modulus ranging from about 50 psi to about 400 psi.

In another aspect of the present invention, a stent-graft is provided comprising a graft body section having a proximal end, a distal end, and defining at least one inflatable porous channel therebetween. A connector member is affixed to the proximal or distal end of the graft body section, the connector member comprising one or more connector elements. A stent comprising one more proximal stent connector elements is coupled to the one or more connector member connector elements. An inflation medium including at least one therapeutic agent is configured to be introduced into the inflatable channel.

In yet another aspect of the present invention, methods for delivering a therapeutic agent are provided. One method comprises providing a graft body section having a proximal end, a distal end, and defining at least one inflatable porous channel. The graft body is implanted in a body lumen. The porous channel is inflated or injected with an inflation medium including at least one therapeutic agent. The graft may be surgically implanted by standard surgical techniques or implanted by endoluminal or other modes of delivery. Typically, the porous channel is inflated before, during, or after graft deployment and/or implantation. The graft delivery system, an example of which is described in more detail in co-pending U.S. patent application Ser. No. 10/686,863, assigned to the assignee of the present application and incorporated herein by reference, is then disconnected and removed from the body, leaving the implant in place for releasing the agent into the body for a period of time thereafter. The therapeutic agent is transported from the inflation medium through the porous channel and the agent is released into the body lumen from a luminal or abluminal surface of the graft body section. The porous channel comprises expanded or perforated polytetrafluoroethylene having varying levels of porosity. The inflation medium comprises a therapeutic agent-carrying host polymer that further releases the therapeutic agent by diffusion or degradation processes. Generally, the graft body section inhibits transport of a bulk of the host polymer. According to the invention, a useful host polymer may comprise polyethylene glycol that is injected as a liquid and has a cure time ranging from about three minutes to about twenty minutes and a post-cure elastic modulus ranging from about 50 psi to about 400 psi.

In still another aspect of the present invention, kits comprising a graft and instructions on how to implant and inflate the graft for delivery of a therapeutic agent are provided. Such kits may also include a source of the inflation medium containing the at least one therapeutic agent. The graft may comprise any of the delivery structures described herein, while the instructions for use will generally recite the steps for performing one or more of the above-described methods. The instructions will often be printed, optionally being at least in part disposed on packaging. The instructions may alternatively be contained in a videotape, compact disk, digital video disk, other machine readable format or code, a graphical representation, or the like showing and/or reciting any of the above-described methods.

The drug delivery mechanism of the present invention may be implanted in a number of different implantable devices. While the discussion above has been directed to grafts and stent-grafts, it will be appreciated that other inflatable porous implant devices may be utilized for the delivery of the therapeutic agents. In particular, inflatable porous bladders may be employed having a saccular or tubular configuration. The bladders are permanent in that they are implantable at a treatment site for an indeterminate and potentially lengthy period of time. The bladders may be applied to the vasculature (e.g., blood vessels) or to other body lumens, organs, and tissue structures in the body such that its presence does not adversely affect any bodily functions, and typically the bladder performs some mechanical function in addition to serving as a drug delivery platform. The bladders may additionally be occlusive, such as for blocking the fallopian tubes, or applied in other capacities, such as for tissue bulking, treatment of urinary incontinence, treatment of cancer, birth control treatment, sinus implant, prosthetic in cosmetic or plastic surgery, supporting spine structure, controlled flow or on-off valve in a lumen or duct, and similar applications.

In one embodiment, an inflatable porous implant suitable for implantation in a human body may generally comprise an inflatable porous bladder having a substantially non-elastic bladder wall defining a volume. At least one bladder wall opening is provided for introduction of an inflation medium including at least one therapeutic agent. At least one bladder wall closure for each of the at least one bladder openings is also provided for maintaining the inflation medium within the volume. The bladder wall and inflation medium may be selected to deliver the desired therapeutic agent to the locale of the implant site. Exemplary inflatable implants that may be utilized with the present invention are described in detail in co-pending U.S. patent application Ser. No. 10/461,853, assigned to the assignee of the present application and incorporated herein by reference. The inflatable porous bladder may comprise any of the materials discussed above with respect to the inflatable porous graft channel as well as employ any of the above-mentioned characteristics with respect to transport and porosity of such implant materials. Similarly, the inflation medium, the therapeutic agent, various modes of release, agent dosages and durations may be used in this embodiment as previously described.

In another embodiment, an occlusive bladder may be positionable at a treatment location or situs in the patient body via a catheter, surgical implantation, or other implantation technique. In this example, the inflation medium could be used to inflate the bladder to occlude the vessel as well as to deliver a therapeutic agent. The agent may comprise thrombotic agents to reduce the risks of leaks around the occludant, cellular in-growth agents to enhance the permanence of the hemostatic seal provided by the occludant, and/or other agents that provide other therapeutic benefits to the tissue surrounding the bladder. The inflation medium may further comprise embolic compositions that serve this dual role of acting as a mechanical obstruction to reduce or block the flow of fluid through the body lumen, and acting as a reservoir of therapeutic agent for local delivery to the region of the target embolization site. The embolic composition may comprise polyethylene glycol diacrylate, ethoxylated trimethylolpropane triacrylate, or polypropylene glycol diacrylate in combination with pentaerthyritol tetra 3 (mercaptopropionate) and a physiologically acceptable buffer solution. Embolic materials that may be used in conjunction with the present invention are described in detail in co-pending U.S. patent application Ser. No. 11/031,311, entitled "Methods, Compositions, and Devices for Embolizing Body Lumens," filed Jan. 7, 2004, the complete disclosure of which is incorporated herein by reference.

In this dual-role embodiment, the therapeutic agent may initially be contained throughout the volume of the embolic composition, and may be contained either as a suspension, a mixture, or by being chemically bonded to one of the components of the embolic composition. The therapeutic agent may be bonded to the backbone or arm of a component of the embolic composition. For example, the therapeutic agent can be bonded to the polyethylene glycol backbone. Some exemplary drugs and methods for attaching the drugs to the embolic composition are described in J. M. Harris, "Laboratory Synthesis of Polyethylene Glycol Derivatives, " Journal of Macromolecular Science-Reviews in Macromolecular Chemistry, vol. C-25, No. 3, pp. 325-373, Jan. 1, 1985; J. M. Harris, Ed., "Biomedical and Biotechnical Applications of Poly(Ethylene Glycol) Chemistry", Plenum, New York, pp. 1-14, 1992; Greenwald et al., "Highly Water Soluble Taxol Derivatives: 7-Polyethylene Glycol Carbamates and Carbonates:", J. Org. Chem., vol. 60, No. 2, pp. 331-336, 1995, Matsushima et al., "Modification of *E. Coli* Asparaginase with 2,4-Bis(O-Methoxypolyethylene Glycol)-6-Chloro-S-Triazine (Activated PEG.sub.2); Disappearance of Binding Ability Towards Anti-Serum and Retention of Enzymic Activity," Chemistry Letters, pp. 773-776, 1980; and Nathan et al., "Copolymers of Lysine and Polyethylene Glycol: A New Family of Functionalized Drug Carriers," Bioconjugate Chem. 4, 54-62 (1993), each of which are incorporated herein by reference. The therapeutic agent could be mixed in with one of the components during manufacturing or could be stored separately and mixed with the other polymer components prior to use. The embolic compositions may be formed by in vivo polymerization by a Michael addition process as described in PCT Publication Nos. WO 00/44808 entitled "Biomaterials formed by Nucleophilic Addition Reaction to Conjugated Unsaturated Groups" to Hubbell and WO 01/92584 entitled "Conjugate Addition Reactions for the Controlled Delivery of Pharmaceutically Active Compounds" to Hubbell et al., the full disclosures of which are incorporated herein by reference.

According to the invention, the inflatable implant having a porous volume (e.g., graft channel or bladder) containing the agent-carrying host polymer has the capability to allow for larger, more precise dosages of agents to be delivered over longer administration periods into the body as the agent-carrying host polymer may, but not necessarily, represent a substantial fraction of a total mass of the implant. The implantable graft and bladder devices of the present invention may also be easier to place or implant in the body since the host polymer may be loaded into the channel or bladder during or after deployment of the implant so that the device may be inserted in a flexible and low-profile state. Once deployed, the implant may be made more rigid by the injection of the inflation medium. Moreover, such inflatable channels or bladders for drug delivery alleviate any concerns that the agent may be abraded off during placement. Further, the graft and bladder implants of the present invention provide a mechanical or structural function in addition to a drug reservoir function in a single integrated structure. For example, the inflated channels and/or cuffs of the graft body may provide a flow conduit in the body. In the case of the bladder, when injected with the inflation medium it may serve to occlude a body lumen or be utilized for tissue bulking.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

DETAILED DESCRIPTION OF THE INVENTION

Figure 1:
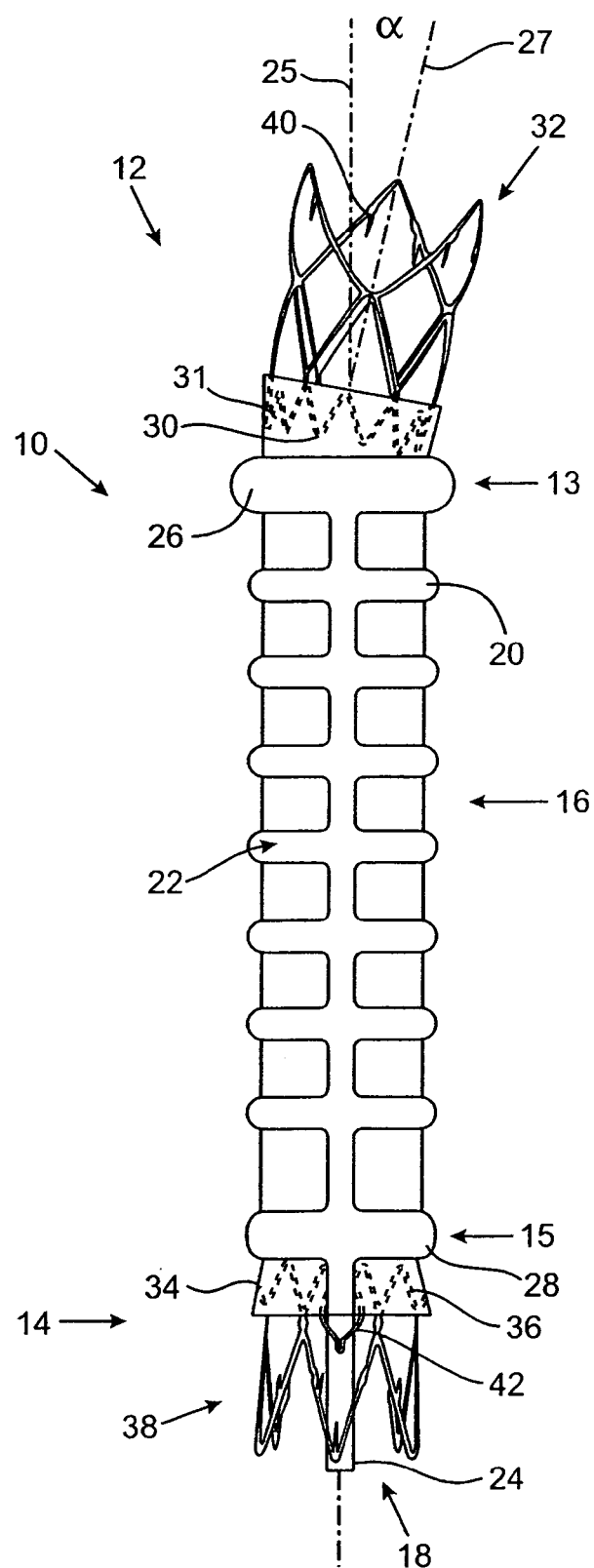
FIG. 1 shows an inflatable porous graft in a deployed configuration according to one embodiment of the present invention.

FIG. 1 shows an inflatable porous graft 10 in its deployed configuration. Unless otherwise stated, the terms "graft" or "stent-graft" are used herein to refer to a prosthesis capable of recreating or reestablishing a natural flow conduit in the diseased vessel or organ to be repaired, replaced, or bypassed, including generally tubular and bifurcated devices and any components attached or integral thereto. For purposes of illustration, the graft embodiments described below are assumed to be most useful in the endovascular treatment of abdominal aortic aneurysms (AAA). For the purposes of this application, with reference to the graft devices, the term "proximal" describes the end of the graft that will be oriented towards the oncoming flow of bodily fluid, typically blood, when the device is deployed within a body passageway. The term "distal" therefore describes the graft end opposite the proximal end. It will be appreciated that the above depictions are for illustrative purposes only and do not necessarily reflect the actual shape, size, dimensions, or particular configurations (cuff, channel, graft shape, connector members, stents, fill port bridges, proximal and distal necks, etc. as well as individual configurations thereof) of the graft 10. As such, the embodiments shown and described herein are merely exemplary and may vary widely while remaining within the scope of the present invention. In addition, although the stent-graft embodiments of the present invention shown herein indicate sealing, stiffness-providing, and other mechanical and clinical benefits of the inflatable channel or channels, such benefits need not be realized to be within the scope of the present invention. For instance, although graft 10 is shown with connector members 30, 36 and stents 32, 38, such features are optional. This applies to all depictions and embodiments herein.

As illustrated in FIG. 1, the graft 10 has a proximal end 12 and a distal end 14 and comprises a tubular structure or graft body section 16. The graft body section 16 has a proximal end 13 and a distal end 15 and forms a longitudinal lumen 18 configured to confine a flow of fluid therethrough and may range in length from about 5 cm to about 30 cm, specifically from about 10 cm to about 20 cm. The graft body section 16 further defines at least one inflatable porous channel 20 or cavity comprising, in this example, a longitudinal channel or spine in fluid communication with a series of approximately parallel circumferential channels or rings. An inflation medium 22 including at least one therapeutic agent 46 is configured to be introduced into the inflatable channel 20 (see FIG. 2).

The channel 20 or channels may enhance the graft body section 16 stiffness upon their inflation, may help to prevent kinking of the graft body section 16, and may also facilitate deployment of the graft 10 within a patient's body passageway. The longitudinal and radial dimensions of the inflatable channel 20 may vary as necessary both among different graft body sections and even within a single graft body section, depending on the indication for which graft 10 is intended to treat. Further, the inflatable channel 20 may be oriented at various angles with respect to the longitudinal axis 25 of graft body section 16, and the channel pitch may vary as necessary.

The inflatable channel 20 or channels may take on longitudinal and/or circumferential configuration or configurations, in any combination, with respect to the graft body section as illustrated. Other orientations such as helical spirals or interconnecting grids or rings may also be suitable alone or in combination with any of the other configurations as well. The inflatable channel or channels may also have a serrated pattern to provide kink resistance or folding resistance. The serrated inflatable channel may be disposed helically, circumferentially, in an annular rib and spine configuration, or the like. Kink resistance of such inflatable channels may be enhanced due to the ability of the serrations to hinge so as to prevent the formation of longitudinal folds. In some instances, the serrations may have differing inner and outer radii. Further, the channels that connect the circumferential rings may alternatively have a staggered or discontinuous longitudinal channel or spine to promote flexibility of the graft body or limb. The longitudinal channel or spine that interconnects the inflatable channels may also take on a non-linear or wave-type configuration so as to allow for improved compression in the graft longitudinal direction. Such a configuration may further reduce the potential for the graft to kink during foreshortening.

A proximal inflatable porous cuff 26 and a distal inflatable porous cuff 28 optionally may be further provided. The proximal and distal cuffs 26 and 28 are in fluid communication with the inflatable channel 20, forming a network of inflatable cuffs and channels in fluid communication with each other. Fill port 24 is in fluid communication with the proximal cuff 26, the distal cuff 28, and the inflatable channel 20, adding to this network for the introduction of the inflation medium 22 into the graft body section 16. The cuffs 26 and 28 may be configured to provide a sufficiently stiff structure when inflated which help to support the graft body section 16 and provide a conformable surface to seal the graft 10 against the interior surface of the vessel in which it is deployed. Sealing helps prevent transmission of hemodynamic pressure to the aneurysm as well as prevents the flow of fluid such as blood around an outer surface of the graft body section 16.

The inflatable cuffs 26 and 28 may be disposed in any number of configurations. For instance, cuffs 26 and 28 may be disposed in an axisymmetric cylindrical pattern, as depicted in FIG. 1, around a proximal end and/or a distal end of the graft body. Alternatively, the proximal and distal sealing cuffs may take on a serrated configuration. Serrated inflatable cuffs have the advantage of not being as susceptible to compression folding so that the graft is less sensitive to changes in the diameter of the body lumen. The serrated inflatable cuffs may comprise a zigzag channel that defines a plurality of apices. When inflated, the serrated inflatable cuffs of the present invention are less sensitive to in-folding that can be caused by diametric interference of the graft with the body lumen. Further, the serrated inflatable cuffs may comprise varying radii in the serrations to further reduce the potential for undesirable in-folding in clinical applications in which in-folding is a possibility.

Configurations in which multiple porous channels, cuffs, or any combination of porous channels or cuffs and non-porous channels or cuffs are present in the same graft body, each or all of which may be separately inflatable with the same or different inflation media, are within the scope of the present invention. For example, an alternative embodiment of a graft body of the present invention (not shown) may comprise one or more relatively non-porous channel or channels that is inflatable with a first inflation medium not having a therapeutic agent. Such a channel or channels serves other functions in the graft body, such as graft sealing, kink-resistance, etc. This same graft body may additionally comprise one or more relatively porous channel or channels, not in fluid communication with the non-porous channel or channels, and that is separately inflatable (through, e.g., one or more separate fill ports) with a different inflation medium carrying a therapeutic agent for delivery to the target area as described herein.

Other configurations in which such a graft body section comprises multiple combinations of a porous and/or non-porous cuff or cuffs that may or may not be in fluid communication with one or more of the porous or non-porous channel or channels are also within the scope of the present invention. For instance, a graft body section may comprise a non-porous proximal and distal cuffs that are in fluid communication with each other through a spine or channel so that they may be inflated with an inflation medium not comprising a therapeutic agent. Such cuffs would primarily serve a sealing function when deployed, for instance, to treat an abdominal aortic aneurysm. Alternatively, the proximal cuff may be made porous and not in fluid communication with the non-porous distal cuff for separate delivery (via a separate fill port) of a different inflation media comprising a therapeutic agent into the proximal region of the graft body section for treatment in a targeted body lumen portion. This graft body section may even further or alternatively comprise, for example, two separately inflatable porous channels that are not in fluid communication with the cuff network or networks. Each of these porous channels may be configured to deliver two different therapeutic agents via different inflation media; alternatively, one of the channels may be non-porous yet not in fluid communication with the cuffs for inflation with a third inflation medium not having a therapeutic agent but having different mechanical properties upon curing to tailor its mechanical function, e.g., to optimize kink-resistance.

Other combinations of multiple, interconnected or separately-networked porous and non-porous cuffs, channels, and their inflation media, etc. are within the scope of the present invention.

The particular configuration shown in FIG. 1 of graft 10 also comprises optional features as follows: a twelve-crown or twelve-apex proximal connector member 30, a two-stage six- and three-crown proximal stent 32, proximal neck portion 31, distal neck portion 34, distal connector member 36, and distal stent 38. Distal connector member 36 and distal stent 38 are analogous to connector member 30 and proximal stent 32 except that the distal stent is a single-stage and its optional barbs face in the opposite, or proximal direction relative to the barbs 40 of proximal stent 32. Distal connector member 36 is affixed or attached to distal stent 38 and the proximal connector member 30 is affixed or attached to proximal stent 32. In turn, proximal and distal connector members 30 and 36 may be attached to, affixed to, formed integrally with tubular structure or graft body section 16, or more typically, with proximal and distal neck portions 31 and 34, respectively. Distal connector member 36 further comprises an optional fill port bridge 42. Proximal neck portion 31 has an inlet axis 27 that forms an inlet axis angle $\alpha$ in relation to graft body section longitudinal axis 25. This angled inlet axis 27 allows the graft to better conform to the morphology of a patient's vasculature in patients who have an angled vessel morphology. The optional connector members 30 and 36 and stents 32 and 38 may be manufactured from conventional medical grade materials.

The network of the inflatable porous channel 20 and cuffs 26 and 28 is inflated, most usefully in vivo, by introduction or injection of a material that may comprise one or more of a solid, fluid (gas and/or liquid), gel or other medium. For example, the inflation medium 22 may comprise a liquid so that it can be loaded into the channel 20 during or after graft 10 deployment. The inflation medium 22 may either remain a liquid after injection or may thereafter solidify into an elastic material that is compliant due to, e.g., a phase change or formation of crosslinks. In the latter case, the inflation medium 22 may comprise a curable liquid having a cure time ranging from about three minutes to about twenty minutes and a post-cure elastic modulus ranging from about 20 psi to about 400 psi.

According to the invention, a useful inflation medium 22 comprises a therapeutic agent-carrying host polymer. The host polymer 22 includes one more materials selected from the group consisting of polyethylene glycol, polyethylene glycol diacrylate, ethoxylated trimethylolpropane triacrylate, pluronic polyoxymer, acrylamide, polyethylene oxide, polyvinyl alcohol, polyethylene-co-vinyl alcohol, polyacrylic acid, polyethylene-co-acrylic acid, polyethyloxazoline, polyvinyl pyrrolidone, polyethylene-co-vinyl pyrrolidone, polymaleic acid, polyethylene-co-maleic acid, polyacrylamide, polypropylene oxide, polyethylene oxide-co-polypropylene oxide, or similar materials, including functionalized derivatives thereof. The inflation medium 22 may further include a buffer such as glycylglycine or N-[2-hydroxyethyl]piperazine-N'-[2-ethanesulfonic acid] (HEPES) as well as a strong nucleophile selected from the group consisting of a thiol or a group containing a thiol. Saline or another inert biocompatible liquid may be added to this three-component inflation medium 22 in amounts up to about sixty percent of the total inflation medium volume. The inflation medium may be capable of being viewed or otherwise detected via various imaging and/or detection modalities, for example, by the addition of an agent to render the inflation medium or a portion thereof visible under magnetic resonance (MR), ultrasound, fluoroscopy, or other imaging modality. For instance, to render the inflation medium 22 visible under fluoroscopy, radiopaque materials such as tantalum, iodinated contrast agents, barium sulfate, etc. may be added to this three-component medium, typically in the buffer.

The therapeutic agent-carrying host polymer 22 may generally comprise any biocompatible material that is capable of being introduced into the inflatable channel 20 before, during, or after graft 10 deployment and/or implantation. For example, if the graft is surgically implanted, the host polymer 22 including the therapeutic agent 46 may be loaded into the device during manufacturing, in a hospital prior to use, during implantation, or after implantation and before surgical access is closed. If the device is implanted via endoluminal techniques, the host polymer 22 including the therapeutic agent 46 may be injected during or after the deployment process.

Figure 2:
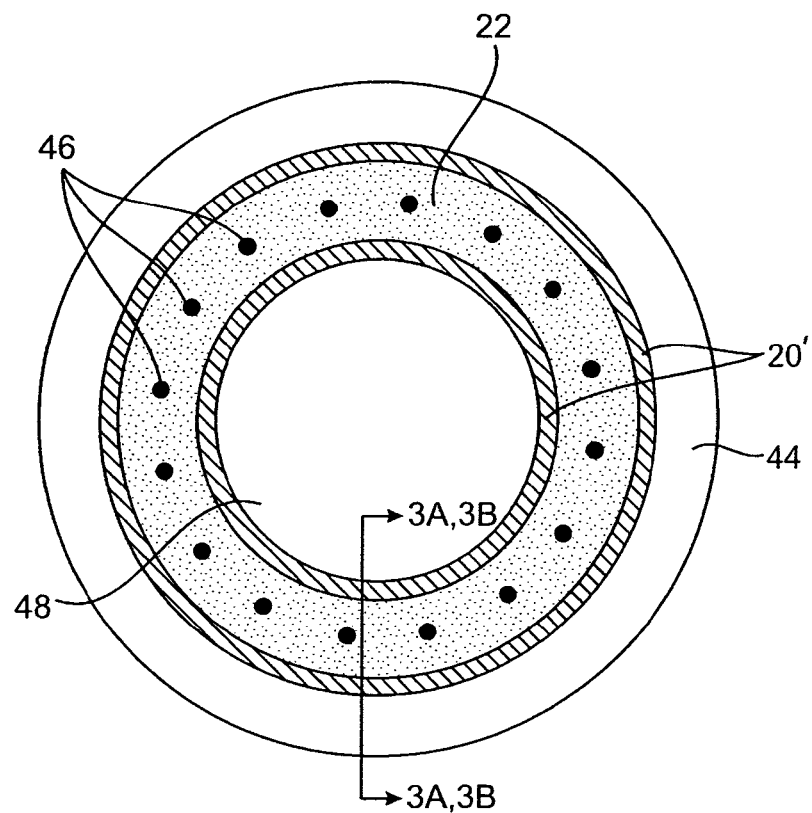
FIG. 2 shows a cross sectional view of an implantable graft in a vessel wall according to another embodiment of the present invention.

Referring now to FIG. 2, a cross sectional view of an implantable graft 10 comprising a circumferential ring channel 20' in a vessel wall 44 having a lumen 48 is illustrated. Delivery of a therapeutic agent 46 may comprise two modes of release. First, the therapeutic agent 46 may be released from the host polymer 22 in a controlled fashion. For instance, the therapeutic agent 46 may be released by diffusion through the host polymer 22. Alternatively therapeutic agent 46 may be released by degradation or decomposition processes, such as for example by hydrolytic degradation of ester or other bonds. It may be preferable for the host polymer 22 to degrade and simultaneously release a therapeutic agent 46 while reducing the mechanical strength and/or stiffness of the graft body section 16 so that the graft 10 becomes more soft or flexible. In such a case, the host polymer 22 may be formulated as a single chain polymer such that when bonds are broken to release the agent, the polymer breaks up as well. In other instances, it may be preferable for the bulk of the host polymer 22 to remain inside the porous channel 20' and not to significantly degrade (e.g., partial degradation). For example, the degradation process may take place predominately at attachment sites of the therapeutic agent to the host polymer located in interstices of the porous channel 20' such that agent release does not necessarily cause significant changes in the host polymer 22. Further, in the case of polymer release via degradation, the graft body section 16 and particularly the channel 20' may comprise biocompatible material capable of inhibiting transport of a bulk of the host polymer 22. In general, a degradation process may be well-suited for delivering relatively large molecules while diffusion may be well-suited for delivering relatively small molecules. However, it will be appreciated that other factors may contribute to the desirability of one process over another.

Figure 3A:
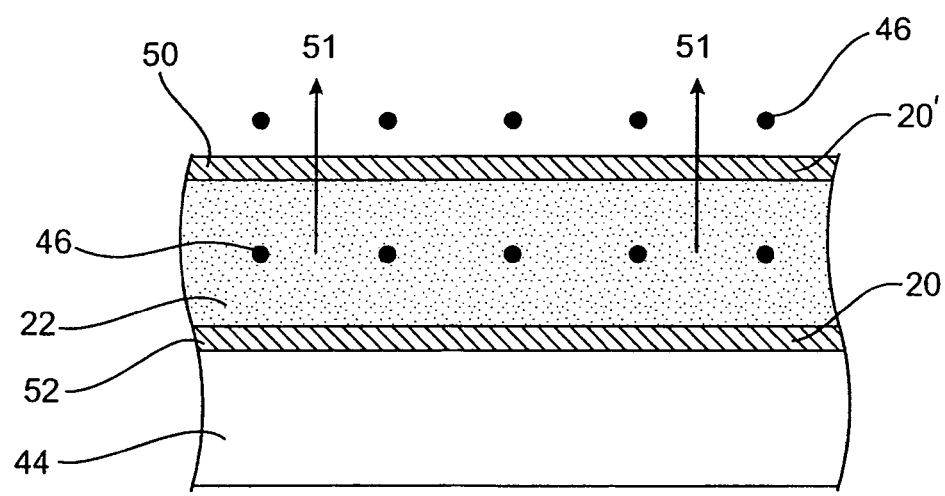
FIGS. 3A and 3B are partial cross sectional views of FIG. 2 illustrating transport of a therapeutic agent.
Figure 3B:
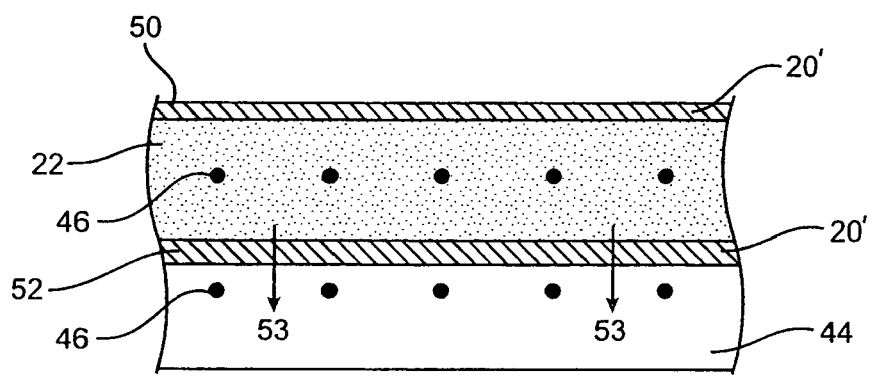

Secondly, the porous channel 20' may be designed to comprise varying levels of porosity, either within or between particular cuffs, channels or cuff/channel segments, so as to provide for controlled and/or programmed drug delivery into the vessel wall or lumen 44, 48 via elution of the agent from pores. In particular, the agent 46 is capable of being transported from the inflation medium 22 through a wall of the porous channel 20' and released into a vessel wall or lumen 44, 48. The agent 46 may be configured to be released into the vessel lumen 48 from a luminal wall 50 of the porous channel 20' as depicted by arrows 51 in FIG. 3A. Alternatively, the agent 46 may be configured to be released into the vessel wall 44 from an abluminal wall 52 of the porous channel 20' as depicted by arrows 53 in FIG. 3B. Another example contemplated by the present invention is one (not shown) in which the porosity along a dimension of a particular cuff or channel 20' (such as length, width, height or any combination thereof) may vary. For instance, such a tailored configuration would be useful in applications in which the drug delivery rate and other properties of the graft or stent-graft (e.g. mechanical properties) may be tailored for the particular clinical needs and indication that is contemplated for that device. In addition, the porosity may be uniform within a particular cuff or channel but different between any given channel and/or cuffs. Any combination of varying porosity within or between given cuffs, channels, or cuff/channel segments is contemplated by the present invention.

The graft body section 16 including the porous channel 20' and cuffs 26 and 28 may comprise any biocompatible material capable of providing transport across its surface. For example, the porous channel 20' may comprise one or more layers of material selected from the group consisting of a fluoropolymer, a polyethyleneterephthalate, a polyvinylchloride, a polyurethane, a polyolefin, and a polyamide. The porous channel 20' may specifically comprise polytetrafluoroethylene, expanded polytetrafluoroethylene, perforated polytetrafluoroethylene, porous polytetrafluoroethylene, or other synthetic material, in any combination. It will be appreciated that the porous channel 20' need not necessarily be mechanically porous. For instance, the channel 20' could be permeable to the therapeutic agent 46 to allow for its transport.

Hence, according to the present invention, porosity of the channel 20' and/or diffusion or degradation characteristics of the host polymer 22 may be modified to achieve a desired release rate for the therapeutic agent 46. For example, the host polymer 22 functional groups and backbone molecular weights may be selected to achieve the desired transport of the agent 46 and mechanical properties of the graft 10. According to the present invention, a useful host polymer 22 comprises the family of functionalized polyethylene glycols. Polyethylene glycol diacrylate may be cross-linked with a compound comprising or containing thiols, such as pentaerthyritol tetra 3 (mercaptopropionate), to form a stable gel which can supply a therapeutic agent 46 by diffusion or by elution from pores of the porous channel 20' and directly into the lumen 48 for direct fluid contact or into, for example, the vessel wall 44 for direct tissue contact. Further, additional functional groups may be added to the polyethylene glycol backbone to allow therapeutic agent 46 release through selective degradation processes. Still further, the host polymer 22 of ethoxylated trimethylolpropane triacrylate may be cross-linked with a compound comprising or containing thiols and functionalized to carry and release therapeutic agents 46.

As discussed above, the host polymer 22 may be injected as a liquid into the porous channel 20' and thereafter solidify due to a phase change or formation of cross-links (i.e., curable liquid). Examples of such host polymers 22 include polymers in the family of pluronic polyoxymers, such as BASF F-127, or acrylamides, with an appropriate lower critical solution temperature such as n-isopropyl polyacrylamide. In the context of curable liquids, the agent 46 may be bound to a monomer of the host polymer 22 which cross-links to create the solid. Subsequently, the bonds linking the agent to the polymer backbone degrade over time at a desired rate based upon several criteria, such as the selection of host polymer materials and type of bonding utilized for agent attachment, so as to allow release of the agent. Alternatively, the agent 46 may be incorporated in an inflation medium comprising one more liquids that solidify and entrap the agent molecules within the host polymer network 22 without any chemical bonds. In this case, the agent may be released over by time by diffusion out to the host polymer network. The rate of diffusion may be based upon several criteria, such as the selection of host polymer materials, density, formulation, polarity of host polymer network, etc.

The at least one agent 46 may comprise a variety of agents that serve any therapeutic purpose depending on the particular indication being treated by the graft. The agent 46 may comprise one or more agents selected from the group consisting of an endothelialization promoting agent (e.g., vascular endothelial growth factor), an angiogenesis promoting agent, an anti-thrombotic agent (e.g., heparin), an anti-aneurysmal agent, an anti-infection agent, an anti-inflammatory agent, an anti-restenosis agent, a chemotherapeutic agent, and an anti-cancer agent. Typically, the quantity of agent releasable into the body lumen ranges in the microgram to milligram levels, roughly from about 10 micrograms to about 100 milligrams. The therapeutic agent is configured to be transported into a body lumen in a time period ranging from about less than a week to about several or many months, roughly from about 7 days to about 12 months.

Figure 4C:
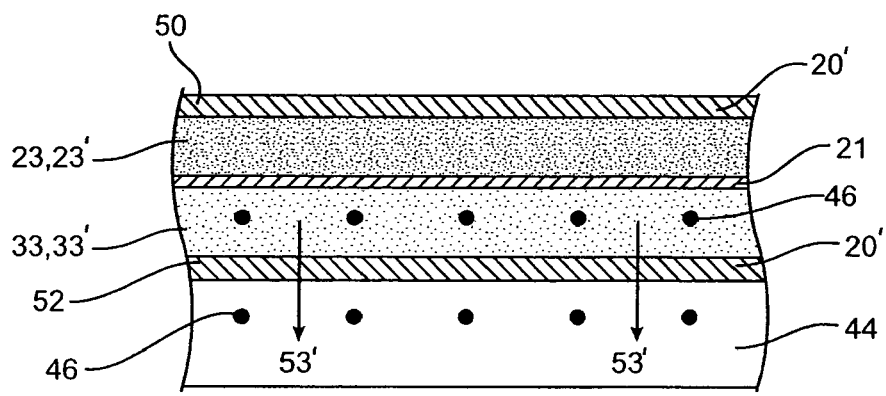
FIGS. 4A-4C are partial cross sectional views of an implantable graft body section having a dual-chamber cuff/channel configuration according to another embodiment of the present invention.
Figure 4A:
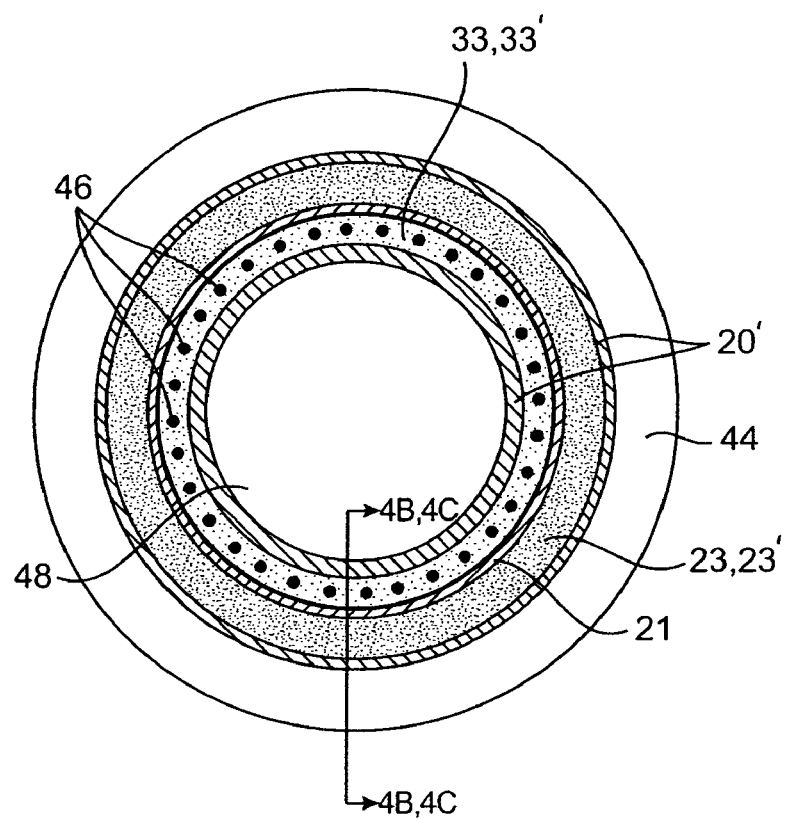
Figure 4B:
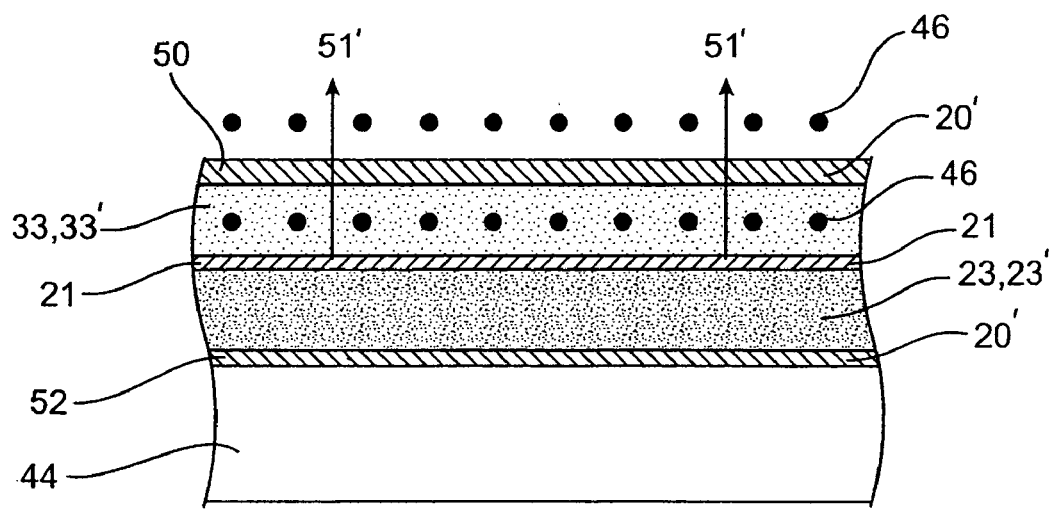

FIGS. 4A-4C illustrate a further embodiment of the present invention. FIG. 4A is a cross sectional view of an implantable graft 10 comprising a circumferential ring channel 20' in a vessel wall 44 having a lumen 48, similar to the embodiment depicted in FIGS. 2, 3A and 3B. In this embodiment, however, circumferential ring channel 20' is a dual-chamber channel, characterized by a relatively non-porous film layer 21 (which comprises, e.g., polytetrafluoroethylene or other suitable material) that divides channel 20' into two chambers 23 and 33. Consistent with other embodiments discussed herein in which multiple inflation media may be included within a single implant or graft body section, two different inflation media 23' and 33' may be separately delivered into each chamber 23 and 33 of channel 20', respectively.

For instance, in the embodiment of FIG. 4B, a first inflation medium 23' containing no therapeutic agent may be directed into chamber 23 such that after or during deposition into chamber 23, as or after medium 23' cures, it swells in a controlled manner such that medium 23' exerts pressure on layer 21, which in turn transmits this pressure to a second inflation medium 33' disposed in chamber 33. Medium 33' comprises a host material containing a therapeutic agent 46. Suitable host materials are those which would allow the therapeutic agent to be transported across or through the wall of chamber 33 and need not be host polymers in this embodiment, and include liquids, solids, gels, and other material forms containing the therapeutic agent. Due to the pressure exerted by the expanding or swelling first inflation medium 23' on the host material 33' via layer 21, therapeutic agent 46 begins to move through host polymer 33' and elute into vessel lumen 48 through the pores of channel 20' as previously described and as depicted by arrows 51'. As shown in FIG. 4C, this same mechanism may work in the other direction: agent 46 and media 23' and 33' may alternatively be configured to facilitate elution of agent 46 into the vessel wall 44 via elution through the abluminal wall 52 of the channel 20', as depicted by arrows 53'.

This "pumping" action driving the release of agent 46 into the vessel lumen 48 or vessel wall 44 may be modulated in a highly controlled fashion so to affect the release of agent 46 in the desired manner. For instance, the formulation, cure or solidification time of media 23' and 33' may individually or collectively be designed to initiate the swelling process and eventual release of agent 46 in a time-delayed fashion. In addition, the rate of swelling may be controlled so as to control the rate of driving force applied to host polymer 33' and thus control the rate of the release of agent 46. For example, swelling of media 23' and/or 33' could be achieved by making the media have an osmotic gradient relative to the in vivo environment. As another example, swelling of media 23' and/or 33' may be achieved by formulating the material as a hydrogel that will take up water after solidification. Swelling of from 10% up to 500% or more can be achieved with this mechanism. Other mechanisms of producing swelling in media 23' and/or 33' may clearly be used.

Although the dual chamber embodiments shown in FIGS. 4A-4C depict a circumferential ring channel configuration with a circumferentially oriented layer 21, as with other embodiments of the present invention it is not necessary that the channel and layer 21 be completely annular as shown or even circumferentially oriented. A dual chamber feature may be included in one or more cuffs or other features of the present invention. In addition, the graft, inflation materials, therapeutic agents, configurations, and methods described herein with respect to other embodiments of the present invention may be used in any combination in the embodiments of FIGS. 4A-4C.

Figure 5:
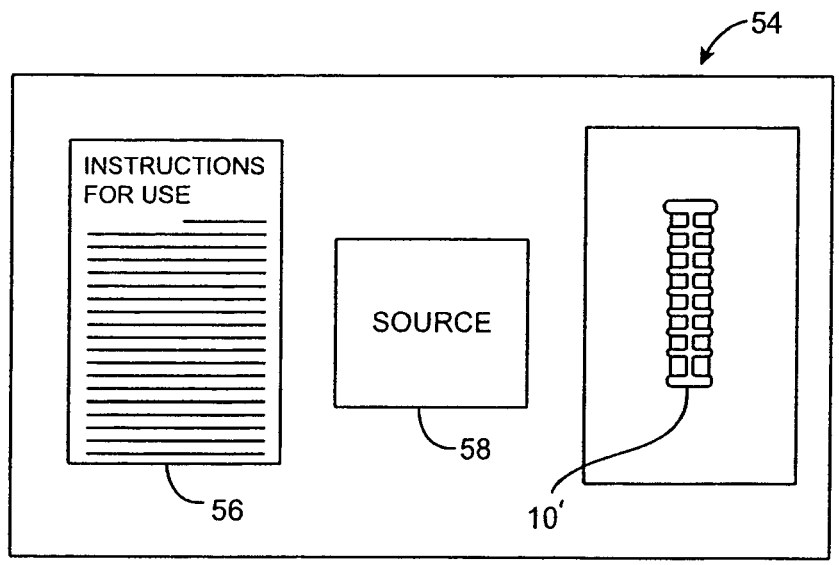
FIG. 5 illustrates a kit according to still another embodiment of the present invention.

Referring now to FIG. 5, this schematic illustrates a kit 54 including a graft 10', its instructions for use 56, and a source 58 of an inflation medium including a therapeutic agent. The graft 10' may comprise any of the structures described herein, including a stent-graft, the source 58 may comprise any of the mediums described herein, and the instructions for use 56 may recite the steps for performing one or more of the above-described methods. The instructions 62 will often be printed but may alternatively be contained in a videotape, compact disk, digital video disk, other machine readable format or code, a graphical representations, or the like showing and/or reciting any of the above-described methods.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A graft comprising:
   a graft body section having a proximal end, a distal end, and defining at least one inflatable porous channel;
   at least one inflatable porous cuff disposed at the proximal or distal end of the graft body section and in fluid communication with the at least one channel, wherein the at least one inflatable porous cuff is disposed in an axisymmetric cylindrical manner around the proximal or distal end of the graft body section; and
   an inflation medium including at least one therapeutic agent configured to be introduced into the inflatable channel;
   wherein the inflation medium comprises a curable liquid comprising a therapeutic agent-carrying host polymer.

2. The graft of claim 1 wherein the agent is capable of being transported from the inflation medium through a wall of the porous channel and released into a body lumen.

3. The graft of claim 2 wherein the agent is configured to be released into the body lumen from a luminal or abluminal surface of the graft body section.

4. The graft of claim 2 wherein the porous channel has varying levels of porosity.

5. The graft of claim 2 wherein the graft body section comprises one or more materials selected from the group consisting of a fluoropolymer, a polyethyleneterephthalate, a polyvinylchloride, a polyurethane, a polyolefin, and a polyamide.

6. The graft of claim 2 wherein the graft body section comprises expanded or perforated polytetrafluoroethylene.

7. The graft of claim 2 wherein a quantity of the agent releasable into the body lumen ranges from about 10 micrograms to about 100 milligrams.

8. The graft of claim 2 wherein the therapeutic agent is configured to be transported into the body lumen in a time period ranging from about seven days to about twelve months.

9. The graft of claim 2 wherein the at least one therapeutic agent comprises one or more agents selected from the group consisting of an endothelialization promoting agent, an angiogenesis promoting agent, an anti-thrombotic agent, an anti-aneurysmal agent, an anti-infection agent, an anti-inflammatory agent, an anti-restenosis agent, a chemotherapeutic agent, and an anti-cancer agent.

10. The graft of claim 1 wherein the therapeutic agent is capable of being released by diffusion through the host polymer.

11. The graft of claim 1 wherein the therapeutic agent is capable of being released by degradation of the host polymer.

12. The graft of claim 1 wherein the graft body section comprises biocompatible material capable of inhibiting transport of a bulk of the host polymer.

13. The graft of claim 1 wherein the host polymer is capable of being introduced into the inflatable channel before, during, or after graft deployment or implantation.

14. The graft of claim 1 wherein the inflation medium has a cure time ranging from about three minutes to about twenty minutes and a post-cure elastic modulus ranging from about 50 psi to about 400 psi.

15. The graft of claim 1 wherein the channel comprises one or more features selected from the group consisting of helical spirals, longitudinal channels, and circumferential rings.

16. The graft of claim 1 wherein the at least one inflatable porous cuff is disposed at the proximal end of the graft body section and further comprising at least one second inflatable porous cuff disposed at the distal end of the graft body section in fluid communication with the at least one channel, wherein the at least one second inflatable porous cuff is disposed in an axisymmetric cylindrical manner around the distal end of the graft body section.

17. A graft comprising:
   a graft body section having a proximal end, a distal end, and defining at least one inflatable porous channel therebetween;
   a connector member affixed to the proximal or distal end of the graft body section, the connector member comprising one or more connector elements;
   a stent comprising one or more proximal stent connector elements coupled to the one or more connector member connector elements wherein the stent comprises a multi-crown configuration; and
   a curable inflation medium including at least one therapeutic agent configured to be introduced into the inflatable channel.

18. The graft of claim 17, wherein the curable inflation medium comprises a curable liquid.

19. The graft of claim 17 wherein the connector member comprises a multi-apex configuration.

20. The graft of claim 19 wherein the connector member comprises a twelve-apex configuration.

21. The graft of claim 17 wherein the stent comprises a three-crown portion.

22. The graft of claim 17 wherein the stent comprises a six-crown portion.

23. The graft of claim 17 wherein the stent comprises a three-crown portion and a six-crown portion.

24. The graft of claim 17 wherein the connector member affixed to the proximal end of the graft body section; and further comprising
   a second connector member affixed to the distal end of the graft body section, the second connector member comprising one or more second connector elements; and
   a second stent comprising one or more proximal second stent connector elements coupled to the one or more second connector member connector elements, wherein the second stent comprises a multi-crown configuration.

25. The graft of claim 17 wherein the at least one therapeutic agent comprises one or more agents selected from the group consisting of an endothelialization promoting agent, an angiogenesis promoting agent, an anti-thrombotic agent, an anti-aneurysmal agent, an anti-infection agent, an anti-inflammatory agent, an anti-restenosis agent, a chemotherapeutic agent, and an anti-cancer agent.

26. A graft comprising:
   a graft body section having a proximal end, a distal end, and defining at least one inflatable porous channel;
   at least one inflatable porous cuff disposed at the proximal or distal end of the graft body section and in fluid communication with the at least one channel, wherein the at least one inflatable porous cuff is disposed in an axisymmetric cylindrical manner around the proximal end of the graft body section;
   a connector member affixed to the proximal or distal end of the graft body section, the connector member comprising one or more connector elements;
   a stent comprising one or more proximal stent connector elements coupled to the one or more connector member connector elements wherein the stent comprises a multi-crown configuration; and
   an inflation medium including at least one therapeutic agent configured to be introduced into the inflatable channel;

wherein the inflation medium comprises a curable liquid.

27. The graft of claim 26 wherein the at least one inflatable porous cuff is disposed at the proximal end of the graft body section and further comprising at least one second inflatable porous cuff disposed at the distal end of the graft body section in fluid communication with the at least one channel, wherein the at least one second inflatable porous cuff is disposed in an axisymmetric cylindrical manner around the distal end of the graft body section.

28. The graft of claim 26 wherein the connector member comprises a multi-apex configuration.

29. The graft of claim 28 wherein the connector member comprises a twelve-apex configuration.

30. The graft of claim 26 wherein the stent comprises a three-crown portion.

31. The graft of claim 26 wherein the stent comprises a six-crown portion.

32. The graft of claim 26 wherein the stent comprises a three-crown portion and a six-crown portion.

33. The graft of claim 26 wherein the connector member affixed to the proximal end of the graft body section; and further comprising
    a second connector member affixed to the distal end of the graft body section, the second connector member comprising one or more second connector elements; and
    a second stent comprising one or more proximal second stent connector elements coupled to the one or more second connector member connector elements, wherein the second stent comprises a multi-crown configuration.

34. The graft of claim 26 wherein the at least one therapeutic agent comprises one or more agents selected from the group consisting of an endothelialization promoting agent, an angiogenesis promoting agent, an anti-thrombotic agent, an anti-aneurysmal agent, an anti-infection agent, an anti-inflammatory agent, an anti-restenosis agent, a chemotherapeutic agent, and an anti-cancer agent.

* * * * *